United States Patent [19]

Urata et al.

[11] Patent Number: 4,576,967

[45] Date of Patent: Mar. 18, 1986

[54] NOVEL POLYOL ETHER COMPOUNDS, PROCESS PREPARING THE COMPOUNDS, AND COSMETICS COMPRISING SAME

[75] Inventors: Koichi Urata; Naotake Takaishi, both of Utsunomiya; Yuji Suzuki, Tokyo, all of Japan

[73] Assignee: KAO Corporation, Tokyo, Japan

[21] Appl. No.: 631,210

[22] Filed: Jul. 16, 1984

[30] Foreign Application Priority Data

Jul. 25, 1983 [JP] Japan .................. 58-135421

[51] Int. Cl.$^4$ .................. A61K 7/00; C07C 43/10; C07C 43/14
[52] U.S. Cl. .................. 514/772; 568/675; 568/679; 568/680; 568/623
[58] Field of Search .............. 568/675, 679, 680, 623; 424/365; 514/772

[56] References Cited

U.S. PATENT DOCUMENTS

| | | | |
|---|---|---|---|
| 2,258,892 | 10/1941 | Harris | 568/679 |
| 3,666,671 | 5/1972 | Kalopissis et al. | 568/679 |
| 4,298,764 | 11/1981 | Berkowitz | 568/680 |
| 4,465,866 | 8/1984 | Takaishi et al. | 568/679 |

FOREIGN PATENT DOCUMENTS 2455286  8/1976  Fed. Rep. of Germany .

Primary Examiner—Howard T. Mars

Attorney, Agent, or Firm—Oblon, Fisher, Spivak, McClelland & Maier

[57] ABSTRACT

Triglycerine monoalkyl ethers of the general formula (I), which are novel polyol ether compounds,

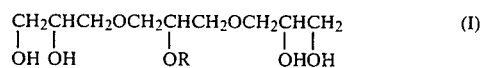
(I)

in which R represents a saturated or unsaturated, linear or branched fatty hydrocarbon group having from 8 to 24 carbon atoms.

The ethers (I) of the present invention are prepared from firstly subjecting 1,3-bis-o-(2,3-o-isopropylideneglyceryl)glycerine (II) and an etherifying agent (IV) to Williamson's ether synthesis reaction, and the resulting 1,3-bis-o-(2,3-o-isopropylideneglyceryl)-2-o-alkylglycerine (III) is subsequently subjected to hydrolysis.

The ethers according to the invention are chemically stable because no linkages susceptible to decomposition, e.g. ester bond, are contained in the molecular structure of the ethers. Moreover, the ethers give a reduced degree of stimulus to the skin and have the surface activity, so that they are useful as an emulsifier, oil (emolient), humectant, thickener and particularly as a component of cosmetics.

5 Claims, No Drawings

NOVEL POLYOL ETHER COMPOUNDS, PROCESS PREPARING THE COMPOUNDS, AND COSMETICS COMPRISING SAME

BACKGROUND OF THE INVENTION (i) Field of the Invention

This invention relates to novel polyol ether compounds, i.e. 1,3-bis-o-(2,3-dihydroxypropyl)-2-o-alkyl (meaning a saturated or unsaturated group) glycerine (which may be hereinafter referred to simply as triglycerine monoalkyl ether). It also relates to a process for producing such ether compounds and cosmetics comprising the compounds.

(ii) Description of the Prior Art

As is known, a great number of polyhydric alcohol derivatives having ether bonds exist in natural fields, of which monoalkyl ethers of glycerine (hereinafter referred to simply as glyceryl ethers) are most popular. For example, lipids of fishes contain palmityl glyceryl ether (hereinafter referred to simply as chimyl alcohol), stearyl glyceryl ether (hereinafter referred to simply as batyl alcohol), and oleyl glyceryl ether (selakyl alcohol).

The glyceryl ethers have a w/o type emulsifying characteristic and thus wide utility as cosmetic substrates (Japanese Laid-open Patent Application Nos. 49-87612, 49-92239 and 52-12109, and Japanese Patent Publication No. 57-36260). It is also known that the glyceryl ethers have the pharmaceutical actions such as an acceleration effect for the blood cells formulation in the marrow, the antiphlogistic action, and the antitumor activity (Japanese Patent Publication Nos. 49-10724 and 52-18171).

In view of the fact that glyceryl ethers which have a number of characteristics are the unique type of surface active agent, attempts have been made to prepare, from polyhydric alcohols, polyol ether compounds similar in molecular structure (i.e. ether bonds and hydrophilic OH groups are contained in the molecule thereof) to glyceryl ethers (U.S. Pat. No. 2,258,892, Japanese Patent Publication No. 52-18170, and Japanese Laid-open Patent Application Nos. 53-137,905 and 54-145,224). The resulting polyol ether compounds which have a w/o type emulsification characteristic are utilized as cosmetic substrates (German Laid-open Patent Publication No. 2,455,287), or are used, aside from an ordinary emulsifier, as an antibacterial agent or antimold agent.

The present inventors paid out attention to the utility of such polyol ether compounds, and already found and proposed in our patent applications (Japanese Laid-open Patent Application Nos. 57-197235, 57-197236, 58-13530 and Japanese Patent Application No. 57-200587) that alkyl glycidyl ethers readily produced from alcohols were used to prepare mono and dialkyl ethers which are polyol ether compounds for use as substrates for various cosmetics.

SUMMARY OF THE INVENTION

We made further studies on the polyol ether compounds and found that triglycerine monoalkyl ethers of the general formula (I), which are novel polyol ether compounds,

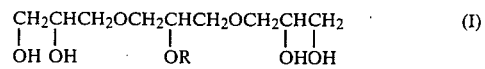

in which R represents a saturated or unsaturated, linear or branched fatty hydrocarbon group having from 8 to 24 carbon atoms, have excellent surface activity. The present invention is accomplished based on the above finding.

Accordingly, an object of the invention is to provide novel polyol ether compounds of the formula (I).

Another object of the invention is to provide a process for producing the compounds (I).

A further object of the invention is to provide cosmetics comprising the compounds (I).

DETAILED DESCRIPTION OF THE INVENTION AND PREFERRED EMBODIMENTS

Glycerine polymers or esters thereof were proposed for use as a surface active agent (e.g. Journal of American Oil Chemist's Society, Vol. 56, pp. 835A-840A, (1979). However, these glycerine polymers or esters thereof are found to be irregular in linkages of glycerine, or to be complicate mixtures having a wide distribution of molecular weight. In contrast, the polyol ether compounds according to the invention have a clear structure in which the ether bond exists at the center of the main chain of a linear trimer of glycerine and are thus novel compounds which completely different from the compounds described in the above literature.

The triglycerine monoalkyl ethers (I) of the present invention are prepared from a known compound of 1,3-bis-o-(2,3-o-isopropylideneglyceryl)glycerine (Journal f. Prakt. Chemie, Vol. 316, pp. 325–326 (1974) according to the process described below in high yield and high purity.

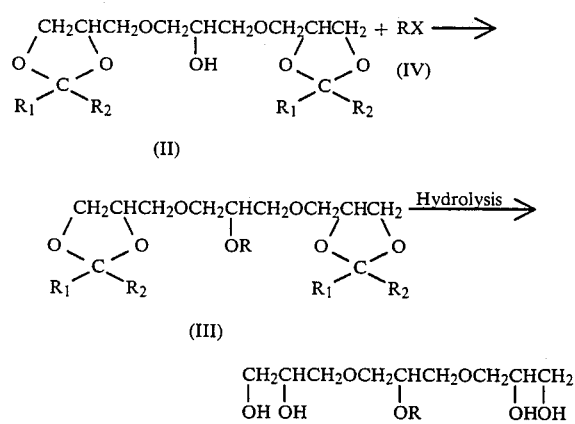

in which R, $R_1$ and $R_2$ have the same meanings as defined before, respectively, and X represents a halogen atom or the like.

More particularly, the known compound of 1,3-bis-o-(2,3-o-isopropylideneglyceryl)glycerine (II) is etherifying in the presence of an alkaline substance and a catalytic amount of a quaternary onium salt (Williamson's ether synthesis), thereby giving 1,3-bis-o-(2,3-o-isopropylideneglyceryl)-2-o-alkylglycerine (III), and hydrolyzing the alkylglycerine to obtain an intended triglyceryl monoalkyl ether (I).

In the first step of the process of the invention, the 1,3-bis-o-(2,3-o-isopropylideneglyceryl)-2-o-alkylglycerine (III) is prepared from the 1,3-bis-o-(2,3-o-isopropylideneglyceryl)glycerine (II) and an etherifying agent (IV). This reaction is the so-called Williamson's ether synthesis reaction, which is preferably carried out in the presence of an alkaline substance and a catalytic amount of a quaternary onium salt.

The etherifying agent (IV: RX) used in the practice of the invention includes, for example, alkyl halides, akylsulfonates, alkylsulfates, and the like. These agents should have a saturated or unsaturated, linear or branched fatty hydrocarbon group having from 8 to 24, and preferably 8 to 18 carbon atoms. More particularly, the agents include alkyl halides such as alkyl chlorides, alkyl bromides, alkyl iodides and the like, alkylparatoluenesulfonates, alkylmethanesulfonates, alkylbenzenesulfonates, and the like. Of these, preferable examples are alkyl bromides. The alkyl moieties of the etherifying agents (IV) include linear fatty hydrocarbon groups such as n-octyl, n-decyl, n-dodecyl, n-tetradecyl, n-hexadecyl, n-octadecyl, n-octadecenyl (oleyl), n-docycyl and the like, branched fatty hydrocarbon groups such as 2-ethylhexyl, 2-hexyldecyl, 2-octyldodecyl, 2-heptylundecyl, 2-(1,3,3-trimethylbutyl)octyl, 2-decyltetradecyl, 2-tetradecyloctadecyl, 5,7,7-trimethyl-2-(1,3,3-trimethylbutyl)octyl, and methyl-branched isostearyl groups represened by the following formula

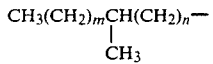

in which m is an integer from 4 to 10, n is an integer from 5 to 11, and m+n is from 11 to 17, with a distribution having a peak at m=7 and n=8. Further, sec-decyl, sec-octyl, sec-dodecyl and the like may be further included. The amount of the etherifying agent may not be critically limited and is generally from 1 to 5 moles, preferably 1 to 2 moles per mole of 1,3-bis-o-(2,3-o-isopropylidene-glyceryl)glycerine (II).

The quaternary onium salts are preferably ammonium salts because of the ease in industrial availability. Examples of the quaternary ammonium salts include: tetraalkylammonium salts such as, for example, tetrabutylammonium chloride, tetrabutylammonium hydrogensulfate, trioctylmethylammonium chloride, lauryltrimethylammonium chloride, stearyltrimethylammonium chloride, benzyltrimethylammonium chloride and the like; a group of alkylammonium salts having a polyoxyalkylene group such as tetraoxyethylene stearyldimethylammonium chloride, bistetraoxyethylene stearylmethylammonium chloride and the like; and betaine compounds, amine oxide compounds, and ion-exchange resins.

These quaternary onium salts may be used in a catalytic amount, or may be used in amounts ranging from 0.005 to 0.5 mole, preferably 0.05 to 0.20 mole, per mole 1,3-bis-o-(2,3-o-isopropylidene-glyceryl)glycerine (II).

In the reaction of the first step, 1.0 mole of 1,3-bis-o-(2,3-o-isopropylideneglyceryl)glycerine (II) is subjected to the reaction in the presence of an aqueous solution of 1 to 10 moles, preferably 3 to 6 moles of an alkaline substance (10 to 80%, preferably 30 to 60% aqueous solution) in an inert hydrocarbon reaction solvent (e.g. hexane, benzene, toluene, xylene or the like) at a temperature from 30° to 70° C., preferably 40° to 60° C. The alkaline substances include, for example, sodium hydroxide, potassium hydroxide, lithium hydroxide or the like. Industrially, sodium hydroxide is preferred.

Next, the resulting 1,3-bis-o-(2,3-o-isopropylideneglyceryl)-2-o-alkylglycerine (III) is subjected to hydrolysis.

The hydrolysis may be conducted by any known techniques. It is preferred to heat the alkylglycerine in an aqueous solution of a protonic acid such as sulfuric acid, hydrochloric acid, nitric acid, phosphoric acid, p-toluenesulfonic acid or the like.

The amount of the protonic acid is from 0.005 to 0.2, preferably from 0.05 to 0.1 mole, per mole of 1,3-bis-o-(2,3-o-isopropylideneglyceryl)-2-o-alkylglycerine (III).

The hydrolysis may proceed in the absence of any reaction solvent, but it is favorable to heat under reflux at a temperature of from 50° to 100° C. using an water-soluble solvent including, for example, a lower alcohol such as THF, dioxane or the like.

In this manner, an intended triglycerine monoalkyl ether (I) can be obtained in high yield.

The triglycerine monoalkyl ether according to the invention is chemically stable because no linkages susceptible to decomposition, e.g. ester bond, are contained in the molecular structure of the ether. Moreover, the ethers give a reduced degree of stimulus to the skin and have the surface activity, so that they are useful as an emulsifier, oil (emolient), humectant, thickener and particularly as a component of cosmetics.

Properties of typical compounds of the present invention are shown below.

TABLE 1

| R in Formula (I) | Color and State (25° C.) | Solubility in Water (25° C.) [30%]* | [70%]* |
|---|---|---|---|
| n-$C_8H_{17}$ | transparent liquid | uniform dissolution | uniform dissolution |
| n-$C_{12}H_{25}$ | white solid | uniform dissolution | formation of liquid crystal |
| n-$C_{16}H_{33}$ | white solid | uniform dissolution | formation of liquid crystal |
| $C_{18}H_{35}$(Oleyl) | light yellow semi-solid | uniform dissolution | formation of liquid crystal |
| iso-$C_{18}H_{37}$ (methyl-branched isostearyl) | light yellow semi-solid | uniform dissolution | formation of liquid crystal |

*Concentrations of the compounds of the invention.

The triglycerine monoalkyl ethers are very hydrophilic and have solubility in water, though nonionic, comparable to ordinary ionic active agents. Because they have the glycerine structure, the compounds of the invention all exhibit high moisture absorptivity but are likely to form liquid crystal because of the long alkyl chain thereof. As a result, once the compound contain water therein, the water is unlikely to be released. Especially, compounds of the formula (I) in which R represents a group containing from 8 to 18 carbon atoms have the well-balanced susceptibility to moisture absorption and unsusceptibility of releasing the moisture. Thus, they have a high moisture effect and are very useful as a humectant of cosmetics.

Of triglycerine alkyl ethers of the invention, those ethers of the formula (I) in which R represents a group having from 14 to 18 carbon atoms have higher emulsifying ability and are thus excellent when used as an emulsifier of emulsion-type cosmetics.

The amount of the ether compounds in cosmetics varies depending on various factors. When used as an emulsifier, the amount is from about 0.2 to 15 wt% and when used as a humectant, the amount is conveniently from 5 to 50 wt%.

The present invention is described in more detail by way of examples and references. The present invention is by no mean limited to these examples, which are described for illustration only.

REFERENCE 1

Synthesis of
1,3-bis-o-(2,3-o-isopropylideneglyceryl)glycerine (II)

(i) Into a 5 liters reactor equipped with a reflux condenser, dropping funnel, thermometer, and agitator were charged 1008 g of a 50% sodium hydroxide aqueous solution (504 g [12.6 mole] as NaOH), 555 g (4.2 moles) of 1,2-o-isopropylidene glycerine, and 1 liter of hexane, followed by agitation. Subsequently, 71.3 g (0.21 mole) of tetrabutylammonium hydrogensulfate was further added and the resulting reaction mixture was kept at 30° C. From the dropping funnel, 583 g (6.3 moles) of epichlorohydrin was dropped portion by portion whereupon heat was generated from the reaction mixture. After cooled appropriately, the reaction mixture was kept at a temperature from 45° to 50° C. The dropping of epichlorohydrin was completed in about 2 hours. The reaction mixture was agitated for further 2 hours at 45° to 50° C. The gas chromatograph of the reaction mixture revealed a disappearance of the 1,2-o-isopropylidene glycerine. Thereafter, the mixture was cooled, from which the hexane phase was collected by separation. The hexane phase was distilled off under reduced pressure to remove the hexane therefrom. By further distillation under reduced pressure, here was obtained 500 g of 1-o-(2,3-epoxypropyl)-2,3-o-isopropylidene glycerine which was a colorless, transparent liquid.

Yield: 63%.

Boiling point: 83° to 85° C./1.3 mmHg (a value in literature: 92° C. to 93° C./2.5 mmHg).

(Literature: Journal f. Prakt. Chemie., Vol. 316, pp. 325 to 336 [1974]).

(ii) Into a 3 liters reactor equipped with the instruments used in (i) of Reference (1) were charged 1653 g (12.5 moles) of 1,2-o-isopropylidene glycerine and 6.8 g ( b 0.125 mole) of sodium methylate, followed by heating and agitating at a temperature of 85° to 100° C. Thereafter, 471 g (2.5 moles) of the 1-o-(2,3-epoxypropyl)-2,3-o-isopropylidene glycerine obtained in (i) of Reference (1) was dropped from the dropping funnel portion by portion in about 3 hours. During the dropping, the reaction mixture was maintained at about 100° C. After completion of the dropping, the mixture was agitated for further 5 hours at the above-indicated temperature. The gas chromatograph of the reaction mixture revealed disappearance of the 1-o-(2,3-epoxypropyl)-2,3-o-isopropylidene glycerine, after which the product was cooled. Subsequently, the 1,2-o-isopropylidene glycerine used in excess was distilled off under reduced pressure, followed by further distillation under reduced pressure to obtain 600 g of colorless, transparent liquid, 1,3-bis-o-(2,3-o-isopropylideneglyceryl)glycerine.

Yield: 80%.

Boiling point: 162° to 168° C./0.7 mmHg.

Boiling point in literature: 173° to 176° C./0.8 mmHg (Same literature as indicated in (i)).

REFERENCE 2

Synthesis of methyl-branched isostearyl alcohol

Into a 20 liters autoclave were charged 4770 g of isopropyl isostearate [Emery 2310, commercially available from Emery Co., Ltd. U.S.A.] and 239 g of copper-chromium catalyst (product of Nikki Co., Ltd.). Hydrogen gas was charged into the reactor under a pressure of 150 kg/cm$^2$ and the reaction mixture was heated up to 275° C. After hydrogenation under 150 kg/cm$^2$/275° C. for about 7 hours, the reaction product was cooled, followed by removing the catalyst residue by filtration to obtain 3500 g of crude product. The crude product was distilled under reduced pressure thereby obtaining 3300 g of colorless transparent isostearyl alcohol as a fraction of 80° to 167° C./0.6 mmHg. The thus obtained isostearyl alcohol (monomethyl-branched isostearyl alcohol) had an acid value of 0.05, a saponification value of 5.5, and a hydroxyl value of 181.4. IR analysis (liquid film) revealed absorptions at 3340 and 1055 cm$^{-1}$ and NMR analysis (CCl$_4$ solvent) revealed an absorption at ($\delta$)=3.50 (broad triplet, —CH$_2$—OH). According to the gas chromatograph, the alcohol was chiefly composed of about 75% of an alcohol whose number of carbon atoms in the alkyl group was 18, with the remainder being made of alcohols having alkyl groups with 14 and 16 carbon atoms. The branched methyl group was located substantially at the center of the main alkyl chain in all the alcohol components.

REFERENCE 3

Synthesis of methyl-branched isostearyl bromide

Into a 5 liters container equipped with a thermometer, reflux condenser, and agitator were charged 813 g (3 moles) of the methyl-branched isostearyl alcohol obtained in Reference 2, 1032 g (6.1 moles) of a 47% hydrogen bromide aqueous solution, and 50.1 g (0.15 mole) of trimethylstearylammonium chloride, followed by heating to 100° to 120° C. in a mantle heater under agitation. After agitation for about 6 hours at the temperature, it was confirmed from gas chromatograph that the peak of the methyl-branched isostearyl alcohol disappeared. The reaction product was cooled and the organic phase was collected by phase separation. To the lower phase (aqueous phase) was added ether (1.5 liters) for ether extraction. The ether phase was collected by phase separation, followed by combining with the organic phase obtained before and adding a hydrogen bicarbonate aqueous solution to neutralize a remaining acid therewith. By phase separation, the ether phase was collected, to which was added Glauber's salt for drying, followed by distilling off the ether under reduced pressure and further distillation under reduced pressure to obtain 800 g of methyl-branched isostearyl bromide.

Yield: 80%.

Boiling point: 145° to 169° C. (0.3 mmHg).

IR (liquid film, cm$^{-1}$): 1200 to 1300, 720, 640, 560.

NMR (CCl$_4$, $\delta$, TMS internal standard): 3.30 (triplet, J=7.0 Hz, —CH$_2$Br).

Elementary analysis: found and in parentheses, calculated for C$_{18}$H$_{37}$BR: C 64.7% (64.85%); H 11.2% (11.19%); Br 24.4% (23.97%).

Average molecular weight (VPO method/HCCl$_3$): 327 (333 as calculated).

EXAMPLE 1

Synthesis of 1,3-bis-o-(2,3-dihydroxypropyl)-2-o-methyl-branched isostearyl glycerine (i) 192 g of a 50% sodium hydroxide solution (96 g [2.4 moles] as NaOH), 128 g (0.4 mole) of the bisdioxolane compound obtained in (ii) of Reference 1 and 400 ml of hexane were charged into a 2 liters reactor equipped with a reflux condenser, thermometer, dropping funnel and agitator, and agitated. To the mixture was further added 13.6 g (0.04 mole) of tetrabutylammonium hydrogensulfate. The reaction mixture was maintained at a temperature of 30° C., followed by dropping 133.4 g (0.4 mole) of the methyl-branched isostearyl bromide obtained in Reference 3 from the dropping funnel portion by portion in about 20 minutes. After completion of the dropping, the reaction mixture was kept at a temperature of 45° to 50° C. and agitated for about 48 hours as it is. From the gas chromatograph of the reaction mixture, it was recognized that the methyl-branched isostearyl bromide disappeared. Thereafter, 500 ml of water was added to the reaction mixture and agitated. The hexane phase was collected by phase separation. The hexane was distilled off under reduced pressure, followed by further distillation under reduced pressure, thereby obtaining 30 g of a fraction having a boiling point of 60° C. to 240° C./1.0 mmHg. This fraction was not an intended compound as confirmed by the gas chromatography, IR and $^1$H-NMR spectrum analyses.

As the distillation residue, there was obtained 200 g of 1,3-bis-o-(2,3-o-isopropylideneglyceryl)-2-o-methyl-branched isostearyl glycerine which was a colorless, transparent liquid.

Yield: 87%.

Elementary analysis: found and in parentheses, calculated for $C_{33}H_{64}O_7$: C: 69.3% (69.19%), H: 11.2% (11.26%), O: 19.5% (19.55%).

IR (liquid film, cm$^{-1}$): 3100 to 2800, 1460, 1380, 1375, 1255, 1215, 1180–1000, 845.

$^1$H-NMR (δ in CDCl$_3$, TMS internal standard)

1.40 (s) ⎫ four isopropylidenemethyl
1.45 (s) ⎭ group 3.45 to 4.45 (m, 17H,

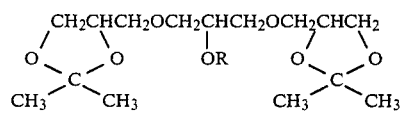

(ii) Into a 2 liters reactor equipped with the same reaction instruments as in (i) of Example 1 were charged 400 ml of ethanol and 400 ml of tap water, followed by further adding 4 g (0.04 mole) of concentrated sulfuric acid. From the dropping funnel, 164.4 g (0.287 mole) of the bisdioxolane obtained in (i) of Example 1 was dropped in about 30 minutes while agitating. After completion of the dropping, the reaction mixture was heated and refluxed. The reaction mixture was opaque at the initial stage of the reaction but are gradually changed into a transparent uniform solution as the hydrolysis proceeded. At about 70° C. a uniform, transparent solution was obtained. Furthermore, the mixture was refluxed at 80° C. for about 3 hours. The reaction product was cooled to room temperature, to which were added 500 ml of ether and then 300 g of a saturated saline solution for ether extraction. The ether phase was collected and the ether was distilled off under reduced pressure. At the time, a viscous gel-like substance was found to be produced simultaneously with violent foaming. Thereafter, the substance was heated and dried at 80° to 90° C./1.0 mmHg. As a result, there was obtained 138 g of 1,3-bis-o-(2,3-dihydroxypropyl)-2-o-methyl-branched isostearylglycerine (triglycerine isostearyl ether) in the form of a light yellow viscous paste.

Yield: 98%.

Elementary analysis: found and in parentheses, calculated for $C_{27}H_{56}O_7$: C: 65.7% (65.82%), H: 11.2% (11.46%), O: 22.8% (22.73%).

Hydroxyl value: 450 (455.5).

IR (liquid film, cm$^{-1}$): 3650–3050, 3000–2700, 1455, 1170–1000, 850.

$^1$H-NMR (δ in CDCl$_3$, TMS internal standard): 3.20 to 4.0 (m, 17H,

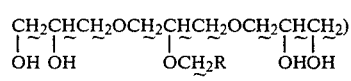

4.0 to 4.4 (broad singlet, 4H, four OHs).

EXAMPLES 2–7

(i) Various 1,3-bis-o-(2,3-o-isopropylideneglyceryl)-2-o-alkylglycerines were prepared according to the procedure (i) of Example 1. The yield and physical values of these compounds are shown in Table 1.

(ii) Various 1,3-bis-o-(2,3-dihydroxypropyl)-2-o-alkylglycerines were prepared according to the procedure (ii) of Example 1. The yield of these compounds were quantitative, with physical values shown in Table 2

TABLE 1

1,3-Bis-O—(2,3-O—Isopropylideneglyceryl)-2-O—Alkyglycerine

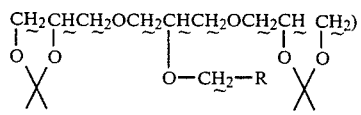

| Example | R | Nature | Elementary Analysis (Calculated) | | | IR(Liquid Film, cm$^{-1}$) |
|---|---|---|---|---|---|---|
| | | | C | H | O | |
| 2 | $C_8H_{17}$ | 195~200° C. | 63.9% | 10.2% | 26.3% | 3050~2700, 1450, 1375, 1365, 1250 |

TABLE 1-continued 1,3-Bis-O—(2,3-O—Isopropylideneglyceryl)-2-O—Alkyglycerine

CH₂CHCH₂OCH₂CHCH₂OCH₂CHCH₂
  \ /          |          \ /
   O   O      OR           O   O
    \C/                     \C/
   /   \                   /   \
  CH₃  CH₃               CH₃  CH₃

| Example | R | Nature | C | H | O | Others |
|---|---|---|---|---|---|---|
| 3 | C₁₂H₂₅ | (0.6 mm Hg) 218~220° C. | 63.86 (66.6) | (10.25) 10.5 | (25.89) 22.9 | 1170~1000, 840 1205 3050~2700, 1450, 1370, 1365, 1250, 1210 |
| 4 | C₁₄H₂₀ | (0.7 mm Hg) liquid | (66.36) 67.4 | (10.73) 10.8 | (22.92) 21.2 | 1175~1000, 840 3100~2700, 1460, 1380 1370, 1255, 1210, 1180 |
| 5 | C₁₆H₃₃ | liquid | (67.40) 67.9 | (10.92) 10.9 | (21.67) 20.6 | ~1000, 840 3050~2700, 1460, 1380 1370, 1250, 1210, 1180 |
| 6 | C₁₈H₃₁ | liquid | (68.34) 69.3 | (11.10) 11.2 | (20.56) 19.9 | ~1000, 840 3050~2700, 1450, 1370 1360, 1245, 1200, 1180 |
| 7 | C₁₈H₃₅ (Oleyl) | liquid | (69.19) 69.7 (69.43) | (11.26) 10.7 (10.95) | (19.55) 19.4 (19.62) | ~1000, 835 3100~2700, 1455, 1380 1370, 1250, 1210, 1180 ~1000, 845 |

¹H—NMR (δ in CDCl₃ TMS Internal Standard)[a]

| Example | Isopropylidene | CH₂CHCH₂OCH₂CHCH₂OCH₂CHCH₂ / OR | Others | Yield (%) |
|---|---|---|---|---|
| 2 | 1.35(s) 1.40(s) | 3.33~4.50(m) | — | 85 |
| 3 | 1.33(s) 1.40(s) | 3.35~4.50(m) | — | 86 |
| 4 | 1.33(s) 1.37(s) | 3.30~4.50(m) | — | 84 |
| 5 | 1.35(s) 1.40(s) | 3.35~4.50(m) | — | 85 |
| 6 | 1.33(s) 1.40(s) | 3.35~4.50(m) | — | 88 |
| 7 | 1.35(s) 1.43(s) | 3.35~4.50(m) | 2.0(br. s,4H) 5.40(t,2H) | 85 |

[a] s: singlet  t: triplet  m: multiplet  br: broad

TABLE 2

1,3-Bis-O—(2,3-Dihydroxypropyl)-2-O—Alkylglycerine

CH₂CHCH₂OCH₂CHCH₂OCH₂CHCH₂
 |   |            |             |   |
 OH OH           OR            OH OH

| Example | R | Nature | C | H | O | Hydroxyl Value (Calculated) | Yield (%) | IR(Liquid Film, cm⁻¹) |
|---|---|---|---|---|---|---|---|---|
| 2 | C₈H₁₇ | liquid | 57.6% (57.93) | 10.2% (10.30) | 31.7% (31.77) | 633.4 (636.8) | 95 | 3700~3050, 3000~2700, 1450, 1170~1000, 850 |
| 3 | C₁₂H₂₅ | liquid | 64.6 (61.73) | 10.5 (10.86) | 27.0 (27.41) | 543.7 (549.3) | 96 | 3700~3050, 3000~2700, 1450, 1170~1000, 850 |
| 4 | C₁₄H₂₀ | mp 35° C. | 63.3 (63.27) | 11.0 (11.08) | 25.2 (25.65) | 518 (514) | 95 | 3700~3050, 3000~2700, 1450, 1170~1000, 850 |
| 5 | C₁₈H₃₀ | mp 40.5° C. | 64.8 (64.62) | 10.9 (11.28) | 23.5 (24.10) | 480 (483) | 95 | 3700~3050, 3000~2700, 1450, 1170~1000, 850 |
| 6 | C₁₈H₃₁ | mp 51° C. | 65.5 (65.82) | 11.3 (11.46) | 22.9 (22.73) | 451.1 (455.5) | 95 | 3700~3050, 3000~2700, 1455, 1180~1000, 855 |
| 7 | C₁₈H₃₅ (Oleyl) | Paste | 65.4 (66.09) | 10.9 (11.09) | 22.4 (22.82) | 456.7 (457.4) | 94 | 3700~3050, 3000~2700, 1455, 1180~1000, 850 |

¹H—NMR(δ in CDCl₃ TMS Internal Standard)[a]

| Example | OH | CH₂CHCH₂OCH₂CHCH₂OCH₂CHCH₂ / OR | Others |
|---|---|---|---|
| 2 | 4.33 (br. s) | 3.33~4.20(m) | — |
| 3 | 4.30 (br. s) | 3.33~4.20(m) | — |
| 4 | 4.10 (br. s) | 3.35~4.0(m) | — |
| 5 | 4.25 (br. s) | 3.35~4.10(m) | — |
| 6 | 3.90 (br. s) | 3.45~3.85(m) | — |

TABLE 2-continued

| 1,3-Bis-O—(2,3-Dihydroxypropyl)-2-O—Alkylglycerine |
|---|
| $\text{CH}_2\text{CHCH}_2\text{OCH}_2\text{CHCH}_2\text{OCH}_2\text{CHCH}_2$ |
| \|  \|         \|         \|  \| |
| OH OH        OR        OHOH |

| | | | |
|---|---|---|---|
| 7 | 4.15 (br. s) | 3.30~4.0(m) | 1.95 (br. s 4H) 5.35 (1, 2H) |

(a)s: singlet t: triplet m: multiplet br: broad

EXAMPLE 8

Triglycerine alkyl ethers were subjected to a test of moisture absorptivity and retentivity (note 1) for evaluation as a humectant. The results are shown in Table 3.

TABLE 3

| | Moisture Absorptivity (%) | | Moisture Retentivity (%) | |
|---|---|---|---|---|
| Compound Tested | after 1 day | after 7 days | after 1 day | after 7 days |
| Products of Invention R in Formula (I) | | | | |
| n-$C_8H_{17}$ | 9.5 | 28.5 | 35 | 10 |
| n-$C_{12}H_{25}$ | 7.0 | 19.5 | 50 | 10 |
| n-$C_{16}H_{33}$ | 5.5 | 17.0 | 65 | 35 |
| $C_{18}H_{35}$ (Oleyl) | 6.0 | 20.0 | 60 | 30 |
| iso-$C_{18}H_{37}$ (Methyl-branched Isostearyl) | 6.0 | 21.0 | 60 | 25 |
| Comparative Products | | | | |
| Sorbitol | 10.5 | 54.0 | 10 | 0 |
| Glycerine | 22.5 | 82.5 | 20 | 5 |

(note 1) *Moisture absorptivity: 1.00 g of a compound being tested which had been dried was placed in a cylindrical glass contained with $\phi$ 2.0 cm×2.0 cm and allowed to stand under constant temperature and humidity conditions of a relative humidity of 93% and a temperature of 25° C. The moisture absorptivity was calculated according to the following equation.

Moisture Absorptivity (%) =

$$\left( \frac{\text{weight of absorbed compound} - \text{weight of dried compound}}{\text{weight of dried compound}} \right) \times 100$$

*Moisture Retentivity: 1.00 g of a compound being tested which contained 10% of moisture was placed in a cylindrical glass container with $\phi$ 2.0 cm×2.0 cm and allowed to stand under constant temperature and humidity conditions at a humidity of 20% and a temperature of 25° C. The variation in the weight was measured and the moisture retentivity was calculated according to the following equation.

Moisture Retentivity (%) =

$$\left( \frac{\begin{array}{c}\text{weight of compound} \\ \text{containing 10\% of} \\ \text{moisture}\end{array} - \begin{array}{c}\text{weight of} \\ \text{moisture released} \\ \text{compound}\end{array}}{\begin{array}{c}\text{weight of compound containing} \\ \text{10\% of moisture} \times 0.1\end{array}} \right) \times 100$$

From the results of this test, it will be seen that the triglycerine alkyl ethers have suitable degree of moisture absorptivity and retentivity and are thus suitable as a humectant of cosmetics.

EXAMPLE 9

Triglycerine monoalkyl ethers and comparative compounds were each subjected to an emulsification test (note 2) to compare them with one another with respect to the performance as an emulsifier. The results are shown in Table 4.

TABLE 4

| | | Stability after 7 Days (%) | |
|---|---|---|---|
| Compounds Tested | State Immediately after Emulsification (Average Size $\phi$) | Oil Phase Separation Rate | Aqueous Phase Separation Rate |
| Products of Invention R in Formula (I) | | | |
| n-$C_{12}H_{25}$ | Slightly nonuniform o/w cream (25 μm) | 4 | 43 |
| n-$C_{14}H_{29}$ | Uniform o/w cream (6.5) | 0 | 12 |
| n-$C_{16}H_{33}$ | Uniform o/w cream (8.5) | 0 | 18 |
| $C_{18}H_{35}$ (Oleyl) | Uniform o/w cream (3.8) | 0 | 10 |
| iso-$C_{18}H_{37}$ (Methyl-branched Isostearyl) | Uniform o/w cream (3.8) | 0 | 8 |
| Comparative Products | | | |
| Diglycerine Monooleate | Uniform w/o cream | 38 | 0 |
| Polyoxyethylene Oleyl Ether | Nonuniform o/w cream | 75 | 88 |

(Note 2) Emulsification test: 5 g of a compound being tested was mixed with 45 g of liquid paraffin and heated at 75° C. Separately, 50 g of purified water was heated to 75° C. and was added to the mixture of the liquid paraffin and the compound under agitation for emulsification, followed by cooling to room temperature while agitating. The emulsion obtained immediately after the emulsification was observed and the state of separation after preservation at 25° C. for 7 days was also observed. The emulsion stability was calculated according to the following equation.

$$\text{separation rate of aqueous phase} = \frac{\text{amount of separated aqueous phase (ml)}}{50} \times 100$$

$$\text{separation rate of oil phase} = \frac{\text{amount of separated oil phase (ml)}}{50} \times 100$$

The above test results demonstrated that while the monoalkyl ester of diglycerine gave a w/o type emulsion, the triglycerine monoalkyl ethers of the invention permitted formation of o/w types emulsions and the emulsifying strength was the highest when the number of carbon atoms in R was from 14 to 18.

EXAMPLE 10

Lotion

Triglycerine monooctyl ether was used to prepare a lotion of the following composition.
(Composition)

| (1) Triglycerine monooctyl ether (product of invention) | 7.0 (wt %) |
|---|---|
| (2) Ethanol | 15.0 |
| (3) Glycine | 1.0 |
| (4) Sodium pyrrolidonecarboxylate | 1.5 |
| (5) Polyoxyethylene lauryl ether | 1.5 |
| (6) Perfume | 0.2 |
| (7) Purified water | balance |

(Preparation)
(1) to (7) were uniformly mixed under agitation. The resulting lotion was applied to skin. It was found that the lotion had good affinity for skin and was soft to the touch, thus being excellent as a cosmetic lotion.

EXAMPLE 11

Emulsion

Triglycerine monolauryl ether was used to prepare an emulsion of the following composition.
(Composition)

| (1) Squalane | 5.0 (wt %) |
|---|---|
| (2) Vaseline | 2.0 |
| (3) Polyoxyethylene oleyl ether | 1.2 |
| (4) Sorbitan sesquioleate | 0.8 |
| (5) Ethanol | 5.0 |
| (6) Triglycerine monolauryl ether (product of invention) | 6.0 |
| (7) 1% Carboxy vinyl polymer aqueous solution | 20.0 |
| (8) Potassium hydroxide | 0.1 |
| (9) Purified water | balance |

(Preparation)
(5), (6), (8) and (9) were mixed and heated to 70° C., which was gradually added, for emulsification under agitation, to (1) to (4) previously mixed and heated. To the mixture was added (7), which was uniformly mixed, followed by uniform emulsification by the use of a homogenizer mixer and cooling to room temperature. The resulting emulsion was applied to skin and was found to give good softness after use. Thus, it had good properties as a cosmetic emulsion.

EXAMPLE 12

Emulsion-type Lip Cream

Triglycerine monocetyl ether was used to prepare an emulsion-type lip cream having the following composition.
(Composition)

| (1) Liquid paraffin | 32 (wt %) |
|---|---|
| (2) Carnauba | 8 |
| (3) Microcrystalline wax | 12 |
| (4) Jojoba oil | 8 |
| (5) Vaseline | 10 |
| (6) Triglycerine monocetyl ether (product of invention) | 5 |
| (7) Glycerine | 5 |
| (8) Purified water | balance |

(Preparation)
(1) to (5) were heated to 85° C. and uniformly mixed, to which was added a heated mixture of (6) to (8), followed by sufficiently agitating for emulsification. Immediately after the emulsification, the mixture was poured into a mold and cooled. The resulting emulsified product was a relatively soft solid w/o emulsion with a glossy, milky white color. When molded as a rod, the emulsion had properties excellent as a lipcream.

EXAMPLE 13

Hand Cream (o/w type)

Triglycerine mono(methyl-branched)isostearyl ether was used as an emulsifier to prepare a hand cream (o/w type) of the following composition.
(Composition)

| (1) Triglycerine mono (methyl-branched) stearyl ether (product of invention) | 3.4 (wt %) |
|---|---|
| (2) Stearic acid | 8.0 |
| (3) Squalane | 4.0 |
| (4) Stearyl alcohol | 1.5 |
| (5) Butyl paraoxybenzoate | 0.1 |
| (6) Methyl paraoxybenzoate | 0.1 |
| (7) Propylene glycol | 5.0 |
| (8) Sodium hydroxide | 0.1 |
| (9) Purified water | balance |

(Preparation)
(1) to (5) were mixed and heated to 75° C. Separately, a mixture of (6) to (9) was heated to 75° C. and was gradually added to the mixture of (1) to (5) for emulsification, followed by cooling to room temperature.

The resulting emulsion was a glossy cream and had a high stability, with good affinity for skin. Thus, it was suitable as a hand cream.

What is claimed is:

1. A polyol ether compound of the general formula (I)

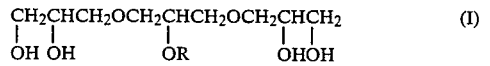

in which R represents a saturated or unsaturated, linear or branched fatty hydrocarbon group having from 8 to 24 carbon atoms.

2. The polyol ether compound according to claim 1, wherein R is a linear fatty hydrocarbon group having from 8 to 18 carbon atoms.

3. The polyol ether compound according to claim 1, wherein R represents a methyl-branched isostearyl group represented by the following formula

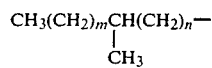

in which m is an integer from 4 to 10, n is an integer from 5 to 11, and m+n is from 11 to 17, with a distribution having a peak at m=7 and n=8.

4. The polyol ether compound according to claim 1, wherein R represents an oleyl group.

5. A cosmetic composition comprising an effective amount of a polyol ether compound of the general formula (I)

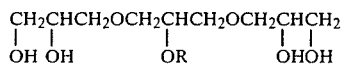

in which R is a saturated or unsaturated, linear or branched fatty hydrocarbon group having from 8 to 24 carbon atoms, and wherein said cosmetic composition is selected from the group consisting of cosmetic creams, emulsions, and lotions.

* * * * *